(12) United States Patent
Shen et al.

(10) Patent No.: US 9,656,256 B2
(45) Date of Patent: May 23, 2017

(54) N-HETEROCYCLIC CARBENE TYPE PALLADIUM CATALYST AND ITS PREPARATION METHOD AS WELL AS APPLICATIONS

(71) Applicant: Shanghai Research Institute of Chemical Industry, Shanghai (CN)

(72) Inventors: An Shen, Shanghai (CN); Yucai Cao, Shanghai (CN); Xiangyang Wu, Shanghai (CN); Xiaofeng Ye, Shanghai (CN); Chen Ni, Shanghai (CN); Yongqing Li, Shanghai (CN)

(73) Assignee: SHANGHAI RESEARCH INSTITUTE OF CHEMICAL INDUSTRY CO., LTD., Shanghai (CN)

( * ) Notice: Subject to any disclaimer, the term of this patent is extended or adjusted under 35 U.S.C. 154(b) by 0 days.

(21) Appl. No.: 14/910,456

(22) PCT Filed: May 28, 2014

(86) PCT No.: PCT/CN2014/078652
§ 371 (c)(1),
(2) Date: Feb. 5, 2016

(87) PCT Pub. No.: WO2015/024403
PCT Pub. Date: Feb. 26, 2015

(65) Prior Publication Data
US 2016/0175828 A1  Jun. 23, 2016

(30) Foreign Application Priority Data
Aug. 22, 2013  (CN) .......................... 2013 1 0370437

(51) Int. Cl.
| | | |
|---|---|---|
| B01J 31/08 | (2006.01) | |
| B01J 31/10 | (2006.01) | |
| B01J 35/08 | (2006.01) | |
| B01J 21/18 | (2006.01) | |
| C07C 201/14 | (2006.01) | |

(Continued)

(52) U.S. Cl.
CPC ........... B01J 31/2273 (2013.01); B01J 31/28 (2013.01); C07C 1/26 (2013.01); C07C 1/321 (2013.01); C07C 1/325 (2013.01); C07C 1/326 (2013.01); C07C 45/68 (2013.01); C07C 49/67 (2013.01); C07C 49/784 (2013.01); C07C 67/343 (2013.01); C07C 209/10 (2013.01); C07C 213/08 (2013.01); C07D 213/16 (2013.01); C07D 265/30 (2013.01); C07D 295/096 (2013.01); C07D 307/36 (2013.01); C07D 333/10 (2013.01); C07D 333/16 (2013.01); C07F 15/006 (2013.01); B01J 2231/4205 (2013.01); B01J 2531/824 (2013.01); C07C 2101/14 (2013.01); C07C 2531/22 (2013.01)

(58) Field of Classification Search
CPC   B01J 31/0237; B01J 31/0205; B01J 31/0225; B01J 31/08; B01J 31/10; B01J 35/08; B01J 35/002; B01J 21/18; B01J 37/0209; B01J 37/084; B01J 2231/342; B01J 2231/4205; B01J 2231/72; C07C 201/14; C07D 301/12; C01B 31/02
See application file for complete search history.

(56) References Cited

U.S. PATENT DOCUMENTS

| | | | |
|---|---|---|---|
| 8,492,552 B2 * | 7/2013 | Ying ..................... | C07F 15/006 252/182.33 |
| 2004/0002489 A1 | 1/2004 | Busacca et al. | |
| 2004/0242947 A1 | 12/2004 | Beller et al. | |

FOREIGN PATENT DOCUMENTS

| | | |
|---|---|---|
| CN | 1564795 | 1/2005 |
| CN | 102627672 | 8/2012 |

(Continued)

OTHER PUBLICATIONS

Peh, Guang-Rong et al., Chemistry—A European Journal (2010), 16 (13), 4010-4017, S4010/1-S4010/72.*

(Continued)

*Primary Examiner* — Alexander R Pagano
*Assistant Examiner* — Ebenezer O Sackey
(74) *Attorney, Agent, or Firm* — Hamre, Schumann, Mueller & Larson, P.C.

(57) ABSTRACT

The present invention relates to an n-heterocyclic carbene (NHC) type palladium catalyst and its preparation method as well as applications. Its preparation process is as below: select glyoxal as the raw material to synthesize glyoxaldiimine in the presence of Lewis acid or Bronsted acid, and then react with paraformaldehyde to get the NHC type ligand. Use palladium$^{(II)}$ to react with the compound containing carbon-nitrogen double bonds to get palladium$^{(II)}$ cyclic dimer; make the palladium cyclic dimer and the NHC type ligand coordinated to get the NHC type palladium catalyst. The palladium catalyst with a brand new structure according to the present invention, boasts high activity and multi-purpose. In addition, it shows excellent reaction activity in a lot of catalytic-coupling reactions including Suzuki-Miyaura, Heck, Buchwald-Hartwig, Kumada-Tamao-Corriu, Sonogashira, Negishi and α-ketone arylation reactions, and some reactions even can be carried out with the presence of an extremely low concentration of catalyst, exhibiting favorable industrialization prospect.

16 Claims, No Drawings

(51) Int. Cl.

| | | |
|---|---|---|
| *C07D 301/12* | (2006.01) | |
| *C01B 31/02* | (2006.01) | |
| *B01J 31/22* | (2006.01) | |
| *B01J 31/28* | (2006.01) | |
| *C07C 67/343* | (2006.01) | |
| *C07D 333/16* | (2006.01) | |
| *C07C 45/68* | (2006.01) | |
| *C07C 49/67* | (2006.01) | |
| *C07C 49/784* | (2006.01) | |
| *C07D 295/096* | (2006.01) | |
| *C07D 307/36* | (2006.01) | |
| *C07F 15/00* | (2006.01) | |
| *C07C 209/10* | (2006.01) | |
| *C07C 1/26* | (2006.01) | |
| *C07C 1/32* | (2006.01) | |
| *C07C 213/08* | (2006.01) | |
| *C07D 213/16* | (2006.01) | |
| *C07D 265/30* | (2006.01) | |
| *C07D 333/10* | (2006.01) | |

(56) References Cited

FOREIGN PATENT DOCUMENTS

| CN | 103418438 | 12/2013 |
|---|---|---|
| DE | 19647584 | 5/1998 |
| DE | 19963009 | 8/2001 |
| EP | 1199292 | 4/2002 |
| JP | 2004-262832 | 9/2004 |
| JP | 2005-008578 | 1/2005 |
| WO | 2004/101581 | 11/2004 |
| WO | 2005/012271 | 2/2005 |

OTHER PUBLICATIONS

Dugger et al., "Survey of GMP bulk reactions in a research facility between 1985 and 2002," Org. Process Res. Dev. 2005, 9, pp. 253-258.

Hassan et al., "Aryl-aryl bond formation one century after the discovery of the Ullmann reaction," Chem. Rev. 2002, 102, pp. 1359-1469.

Corbet et al., "Selected patented cross-coupling reaction technologies," Chem. Rev. 2006, 106, pp. 2651-2710.

Shen et al., "Highly reactive, general and long-lived catalysts for palladium-catalyzed amination of heteroaryl and aryl chlorides, bromides, and iodides: scope and structure-activity relationships," J. Am. Chem. Soc. 2008, 130, pp. 6586-6596.

International Search Report for PCT/CN2014/078652, dated Aug. 22, 2014, and English translation thereof, 6 pages total.

Shen et al.: "Novel monoligated imine-Pd-NHC complexes: extremely active pre-catalysts for Suzuki-Miyaura coupling of aryl chlorides.," Tetrahedron Letters, vol. 55, Apr. 23, 2014, pp. 3278-3282.

\* cited by examiner

N-HETEROCYCLIC CARBENE TYPE PALLADIUM CATALYST AND ITS PREPARATION METHOD AS WELL AS APPLICATIONS

BACKGROUND OF THE INVENTION

1. Technical Field

The present invention relates to a palladium catalyst with a new structure and its preparation as well as applications, and more especially to a multi-purpose, high-activity n-heterocyclic carbene (NHC) type palladium catalyst with a brand new structure, and its preparation as well as purposes in a plurality of coupling reactions.

2. Description of Related Art

Transition metal catalyzed C—C bond coupling reaction is a very effective organic synthesis means through which C—C bond can be formed at specific location under relatively mild conditions. Therefore, it can be applied in the synthesis of a variety of natural products, drug intermediates and organic materials, being of great significance to both academic research and industrialized development. Among these, transition metal palladium catalyzed cross-coupling reaction grows especially fast (Org. Process Res. Dev. 2005, 9, 253).

Organic metal palladium catalysts keep being developed over the years, leading to revolutionary changes of transition metal catalyzed C—C bond coupling reaction. Under the action of these new-type catalysts, aromatic halides, class of aromatic halides, alkenyl halides and the like can have good coupling reaction with various alkene, alkyne, aromatic compounds or organic metallic reagents. Wide functional group tolerance and mild reaction condition exhibit favorable industrialization potential. However, how to reduce catalyst dosage is a vital problem.

According to known literature reports (Chem. Rev. 2002, 102, 1359), a majority of cross-coupling reactions use a catalyst dosage of 1%-10% (U.S. Pat. No. 2,004,002,489, 2002; JP. Patent 2004,262,832, 2003; JP. Patent 2005,008,578, 2003; WO. Patent 2004,101,581, 2004; WO. Patent 2005,012,271, 2004, etc.). However, failure to reduce catalyst dosage to below 1000 ppm has a great negative effect on the product cost and the control of residue of heavy metals in final products (Chem. Rev. 2006, 106, 2651). Few literatures and patents report the use of traces of palladium catalyst to realize coupling reaction. Some excerpts are as below:

In 1991, Syntec reported that, with tri-silyl phosphate as the ligand, under the catalysis of 1000 ppm of palladium acetate, Buchwald reaction occurs between aryl bromide and amine, and the yield is high up to 91%. However, the only drawback is the need of 1 mol % of the ligand (DE. Patent 19,963,009, 1991).

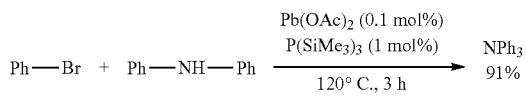

In 1996, Hoechst published a patent about using traces of palladium catalyst to realize Heck reaction, in which the conversion of high yield is realized by means of the dosage of 500 ppm of catalyst for several different kinds of substrates (DE. Patent 19,647,584, 1996).

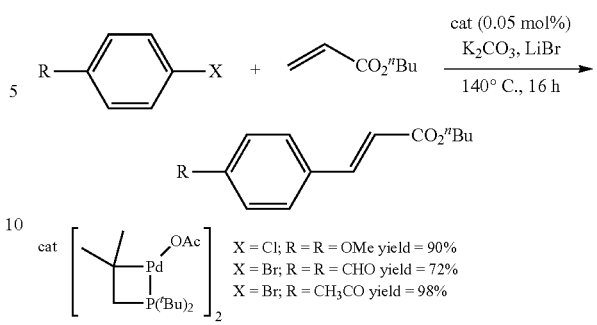

In 2001, OMG and Beller jointly developed a new-type palladium alkene coordinated catalyst to be used for Suzuki coupling reaction of chlorinated aromatic hydrocarbon and boracic acid. This catalyst is especially suitable for reaction using 2-chlorobenzonitrile as the substrate. With a dosage of 500 ppm of catalyst, the yield of this reaction can reach more than 90%. While using p-chlorofluorobenzene and p-chloroanisole as the substrate for reaction, the effect is very general (EP Patent 1,199,292, 2001).

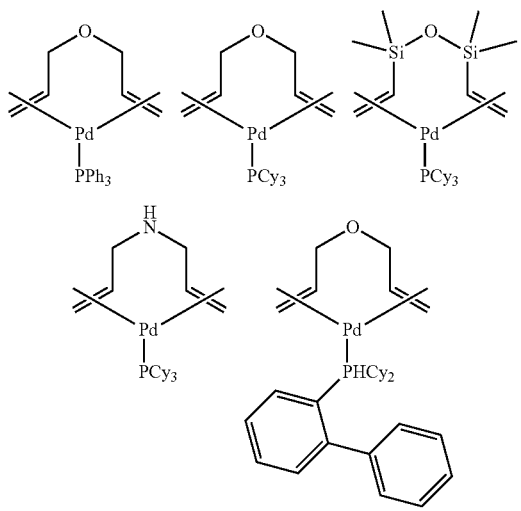

In 2008, Hartwig et al. reported a ferrocene structure based coordination. By using it in combination with palladium acetate, a small amount of 50-2000 ppm of catalyst is enough to catalyze aryl iodide, aryl bromide and even chlorinated aromatic hydrocarbon for Buchwald-Hartwig reaction, and the yield can be high up to over 90% (*J. Am. Chem. Soc.* 2008, 130, 6586).

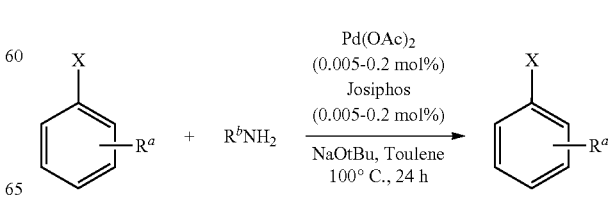

-continued

X = Cl, Br, I

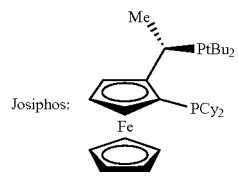

Josiphos:

Thus it can be concluded that, the industrialized application of cross-coupling reaction highly depends on the synthesis of high-efficiency catalyst, and either an improved catalyst on the basis of the original catalyst or a catalyst with a brand new structure is of great importance.

BRIEF SUMMARY OF THE INVENTION

The objective of the present invention is, by overcoming the defects existent in the prior art, to provide a multi-purpose, high-activity n-heterocyclic carbene (NHC) type palladium catalyst with a brand new structure and its preparation as well as applications, especially capable of realizing 7 types of cross-coupling reactions including Suzuki-Miyaura, Heck, Buchwald-Hartwig, Kumada-Tamao-Corriu, Sonogashira, Negishi and α-ketone acylation reactions with a dosage of catalyst less than 500 ppm.

The objective of the present invention is realized through the following technical solution:

The molecule structure of the NHC type palladium catalyst is as below:

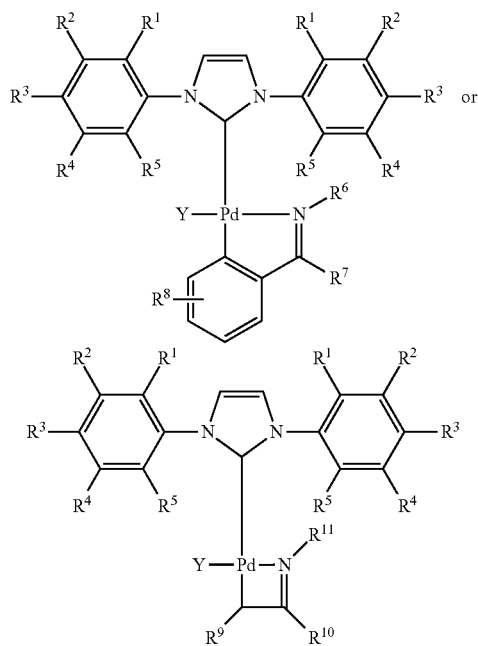

$R^1$, $R^2$, $R^3$, $R^4$ and $R^5$ in the molecule structure above respectively represent H, alkyl, heteroalkyl or aryl independently; $R^6$, $R^7$ and $R^8$ respectively represent H, alkyl, heteroalkyl or aryl independently; $R^9$ represents alkyl or arylalkenyl, $R^{10}$ and $R^{11}$ respectively represent H, alkyl, heteroalkyl or aryl independently; and Y represents Cl or OAc.

$R^1$, $R^3$ and $^5$ respectively represent H, $C_1$-$C_{15}$ linear or branched alkyl and $C_1$-$C_{15}$ aza-, oxa-linear or branched alkyl independently, H, $C_1$-$C_{10}$ linear or branched alkyl and $C_1$-$C_{10}$ aza-, oxa-linear or branched alkyl preferably.

The $C_1$-$C_{10}$ linear or branched alkyl and $C_1$-$C_{10}$ aza-, oxa-linear or branched alkyl contains H, methyl, ethyl, isopropyl, isobutyl, 1-ethylpropyl, 1-phenylpropyl, cyclohexyl, N-dimethyl, N-diethyl, methoxyl and ethyoxyl.

As a preferred embodiment, $R^6$ represents the substituents on benzene ring at different positions, including H, F, 2-methyl, 4-methyl, 3,5-dimethyl, 2-methoxyl, 4-methoxyl, 3,5 dimethoxy, 4-tert-butyl, 3,5-di-tert-butyl, 2-nitryl, 4-nitryl, 4-cyano, 3,4-(methylenedioxy), 4-benzoyl, 4-carbethoxy, 4-trifluoromethyl, phenyl (can be linked to fused ring compound); $R^7$ and $R^8$ respectively present H, hydroxyl, alkoxy, $C_1$-$C_{10}$ linear or branched alkyl, substituted or unsubstituted $C_6$-$C_{18}$ aryl independently, wherein the $C_6$-$C_{18}$ aryl includes phenyl, 1-naphthyl, 4-tert-butyl-phenyl, 3,5-di-tert-butyl-phenyl, 4-methylphenyl, 3,5-dimethylphenyl, 4,4'-biphenyl or 3,5-diphenyl-phenyl.

As a preferred embodiment, $R^9$ represents H, $C_1$-$C_{10}$ linear or branched alkyl or alkenyl, allyl, preferably H, methyl and methylene; $R^{10}$ and $R^{11}$ respectively represent H, hydroxyl, alkoxy, $C_1$-$C_{10}$ linear or branched alkyl, substituted or unsubstituted $C_6$-$C_{18}$ aryl independently, wherein the $C_6$-$C_{18}$aryl includes phenyl, 1-naphthyl, 4-tert-butyl-phenyl, 3,5-di-tert-butyl-phenyl, 4-methylphenyl, 3,5-dimethylphenyl, 4,4'-biphenyl or 3,5-diphenyl-phenyl.

The preparation method of the NHC type palladium catalyst comprises the following steps:

A. Glyoxal used as the raw material reacts with primary amino compound indicated in Formula (I) in the presence of Lewis acid or Bronsted acid to get glyoxaldiimine intermediate compound indicated in Formula (II).

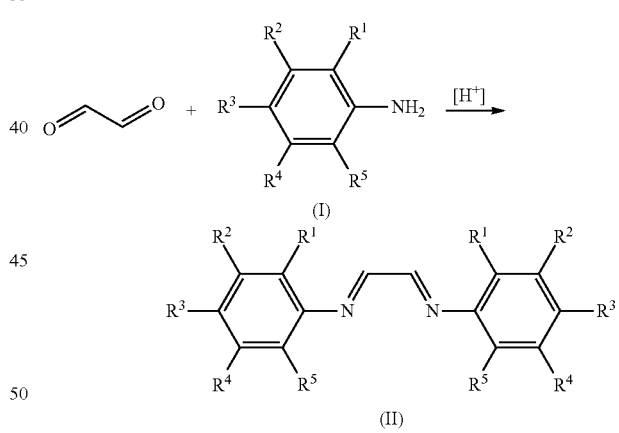

B. The glyoxaldiimine intermediate compound indicated in Formula (II) and paraformaldehyde, under the action of additive (III), are cyclized to form the NHC type compound indicated in Formula (IV).

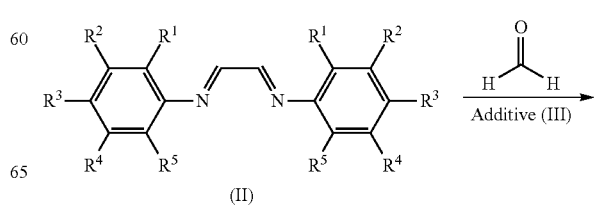

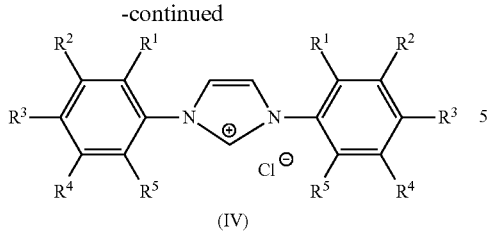

(IV)

C. Palladium$^{(II)}$ and the compound containing carbon-nitrogen double bonds indicated in Formula (VI) or (VII), under the action of inorganic salt (V), are used to get palladium$^{(II)}$ cyclic dimer indicated in Formula (IX).

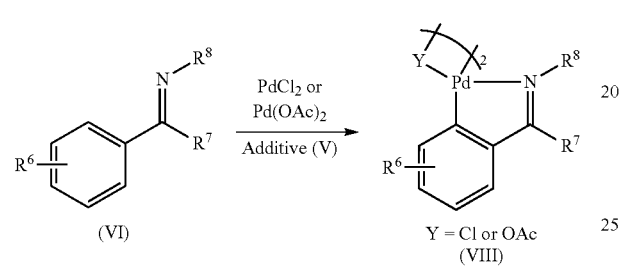

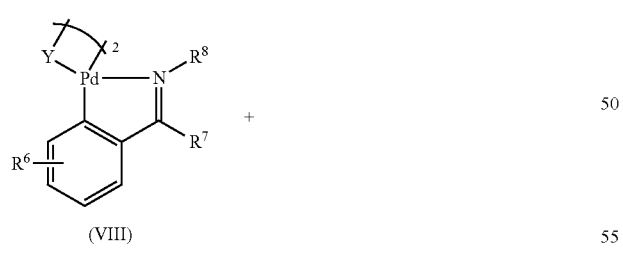

D. The palladium$^{(II)}$ cyclic dimer indicated in Formula (VIII) or (IX) and the NHC type compound indicated in Formula (IV), under alkaline condition, are coordinated to get the NHC type palladium catalyst indicated in Formula (X) or (XI).

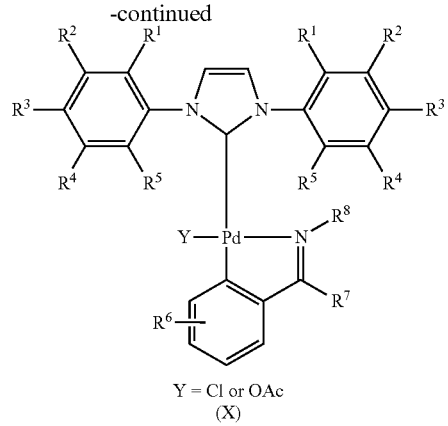

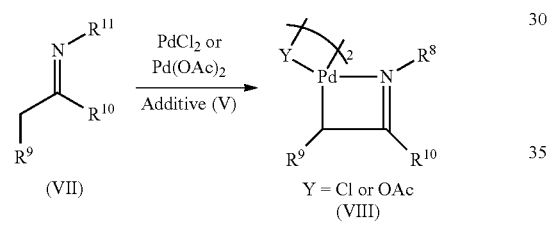

The Lewis acid or Bronsted acid in Step A is selected from one of aluminum trichloride, tin tetrachloride, potassium bisulfate, formic acid, acetic acid, trifluoroacetic acid and tetraethyl titanate.

The cyclization in Step B is the reaction of the glyoxal-diimine intermediate compound indicated in Formula (II) and paraformaldehyde under the action of additive (III). The additive (III) is dioxane hydrochloride solution or trimethyl chlorosilane, preferably trimethyl chlorosilane.

The palladium$^{(II)}$ in Step C is selected from one or the mixture of any two of palladium chloride, palladium acetate, palladium nitrate and palladium acetylacetonate. The inorganic salt (V) is lithium chloride, sodium bromide, sodium iodide or sodium acetate, preferably lithium chloride or sodium acetate.

The coordination in Step D shall be conducted in air-isolated condition. The base required in alkaline condition is selected from one of potassium tert-butoxide, sodium tert-butoxide, potassium hydroxide, sodium ethoxide, potassium carbonate or sodium acetate.

The NHC type palladium catalyst obtained can be applied in coupling reactions of Suzuki-Miyaura, Heck, Buchwald-Hartwig, Kumada-Tamao-Corriu, Sonogashira, Negishi and α-ketone acylation.

The application of the NHC type palladium catalyst in Suzuki-Miyaura reaction catalyzes the cross-coupling reaction of different halogenated aromatic hydrocarbons and arylboronic acid under the action of base, as shown in Formula E:

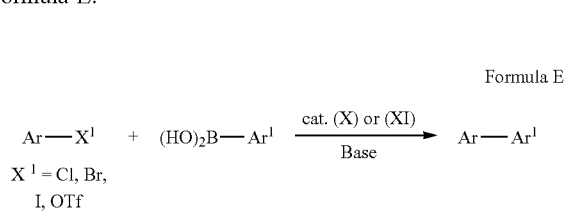

Formula E

Where, Ar and Ar' respectively represent substituted or unsubstituted $C_6$-$C_{18}$aryl, $C_4$-$C_{10}$ aza-polycyclic aromatic hydrocarbon, oxa-polycyclic aromatic hydrocarbon or thiox-polycyclic aromatic hydrocarbon, $X_1$ uses preferably Cl or Br, the base used includes potassium tert-butoxide, sodium tert-butoxide, potassium hydroxide, sodium hydroxide, potassium phosphate, potassium carbonate, sodium carbonate or sodium methoxide.

The application of the NHC type palladium catalyst in Heck reaction catalyzes the coupling reaction of different halogenated aromatic hydrocarbons and alkene, as shown in Formula F:

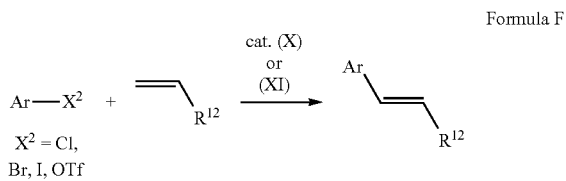

Formula F

Where, Ar represents substituted or unsubstituted $C_6$-$C_{18}$ aryl, $R_{12}$ represents substituted or unsubstituted $C_6$-$C_{18}$aryl, ester or benzyl containing methyl ester, ethyl ester, isopropyl ester and tert-butyl ester, and $X_2$ preferably uses Cl or Br.

The application of the NHC type palladium catalyst in Buchwald-Hartwig reaction catalyzes the reaction of different halogenated aromatic hydrocarbons and primary or secondary amine under the action of base, as shown in Formula G:

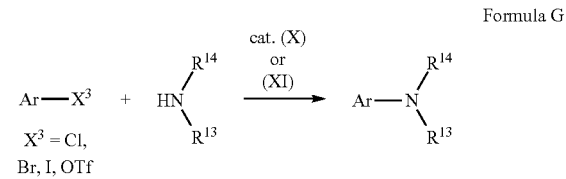

Formula G

Where, Ar represents substituted or unsubstituted $C_6$-$C_{18}$ aryl, $R_{13}$, $R_{14}$ respectively represent H, $C_1$-$C_6$ alkyl or cycloalkyl, substituted or unsubstituted $C_6$-$C_{18}$aryl, or linked pyranoid carbocycle, pyranoid oxa-carbocycle, pyranoid aza-carbocycle independently, $X_3$ preferably uses Cl or Br, and the base used includes potassium tert-butoxide, sodium tert-butoxide, potassium hydroxide, sodium hydroxide, potassium phosphate, potassium carbonate, sodium carbonate or sodium methoxide.

The application of the NHC type palladium catalyst in Sonogashira reaction catalyzes the coupling reaction of different halogenated aromatic hydrocarbons and terminal alkyne under the action of base, as shown in Formula H:

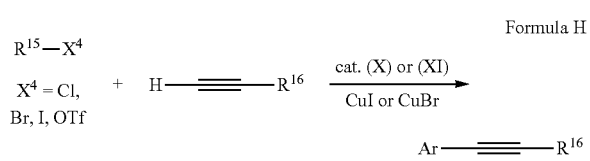

Formula H

Where, $R_{15}$ represents $C_1$-$C_{10}$alkyl, cycloalkyl, $R_{16}$ represents substituted or unsubstituted $C_6$-$C_{18}$aryl, $C_1$-$C_{10}$linear alkyl, branched alkyl or cycloalkyl or alkoxy, $X_4$ preferably uses Br, and the base used includes potassium tert-butoxide, sodium tert-butoxide, potassium hydroxide, sodium hydroxide, potassium phosphate, potassium carbonate, sodium carbonate or sodium methoxide.

The application of the NHC type palladium catalyst in Kumada-Tamao-Corriu reaction catalyzes the coupling reaction of different halogenated aromatic hydrocarbons and aryl Grignard reagent, as shown in Formula I:

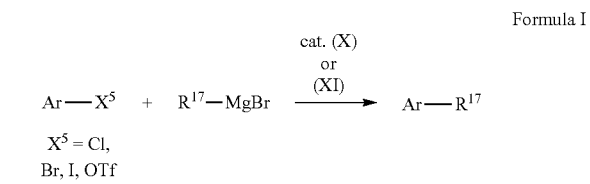

Formula I

Where, Ar represents substituted or unsubstituted $C_6$-$C_{18}$ aryl, $R_{17}$ represents substituted or unsubstituted $C_6$-$C_{18}$aryl, furanoid or pyranoid aza-heterocyclic aryl, furanoid or pyranoid oxa-heterocyclic aryl or furanoid thia-heterocyclic aryl, and $X_5$ preferably uses Cl or Br.

The application of the NHC type palladium catalyst in Negishi reaction catalyzes the coupling reaction of different halogenated aromatic hydrocarbons and organic zinc reagent, as shown in Formula J:

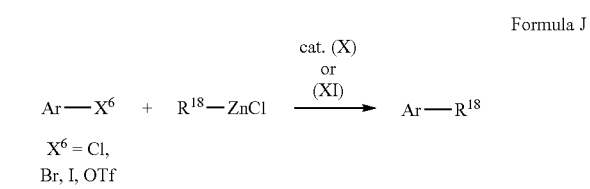

Formula J

Where, Ar represents substituted or unsubstituted $C_6$-$C_{18}$ aryl, $R_{18}$ represents substituted or unsubstituted $C_6$-$C_{18}$aryl, benzyl or homoallyl, and $X_6$ preferably uses Cl or Br.

The application of the NHC type palladium catalyst in α-ketone arylation reaction catalyzes the coupling reaction of different halogenated aromatic hydrocarbons and α-ketone, as shown in Formula K:

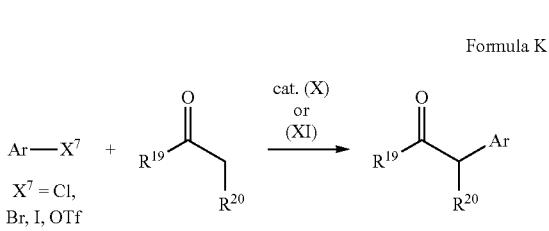

Formula K

Where, Ar represents substituted or unsubstituted $C_6$-$C_{18}$aryl, $R_{19}$ represents substituted or unsubstituted $C_6$-$C_{18}$aryl, furanoid or pyranoid aza-heterocyclic aryl, furanoid or pyranoid oxa-heterocyclic aryl or furanoid thia-heterocyclic aryl, $R_{20}$ represents $C_1$-$C_6$ linear alkyl, branched alkyl or cycloalkyl. Wherein $R_{19}$ and $R_{20}$ can be linked to ring, $X_7$ preferably uses Cl or Br, and the base used includes potassium tert-butoxide, sodium tert-butoxide, potassium hydroxide, sodium hydroxide, potassium phosphate, potassium carbonate, sodium carbonate or sodium methoxide.

Comparing with the catalysts in the existing reports, the NHC type palladium catalyst with a brand new structure synthesized according to the present invention has the following features:

(1) High activity. The catalyst uses electron-very-rich NHC as part of ligand, not only improving the activity of the catalyst and quickening the reaction speed of oxidative addition in coupling reaction, but also greatly increasing the stability of the catalyst to air due to the characteristics of the NHC type ligand. On the other hand, the utilization of imine structure as the balancing ligand of the catalyst for the first time, by modifying the substituent group on the imine benzene and changing the substituent group on the imine nitrogen atom. This significantly enriches the adjustability of the balancing ligand, providing possibility to further adjust the activity of the catalyst.

(2) Multi-purpose. Just because of the very high catalytic activity of the catalyst for the present invention and further adjustability of the catalytic activity, the present invention can be applied in 7 types of common catalytic coupling reactions including Suzuki-Miyaura, Heck, Buchwald-Hartwig, Kumada-Tamao-Corriu, Sonogashira, Negishi and α-ketone arylation. In particular, good effect can be also achieved in the presence of a very small amount of the catalyst (less than 500 ppm), showing promising industrialized application prospect.

DETAILED DESCRIPTION OF THE INVENTION

The present invention is detailed in combination with the embodiments below.

Embodiment 1

Synthesis of N,N'-Bis(2,6-Diisopropylphenyl)Ethanediimine

Add 36.3 g of glyoxal (0.25 mol, 40% aqueous solution), 350 mL of ethanol, 88.5 g of 2,6-diisopropylphenylamine (0.5 mol) and 1.15 g of formic acid (0.025 mmol) in a reactor, and keep mixing for 3 h for reaction at the ambient temperature (15-20° C.). Filter the resultant reaction liquid, wash the filter cake with 150 mL of methanol, and then dry the filter cake to constant weight to get the N,N'-Bis(2,6-diisopropylphenyl)ethanediimine. The product is bright yellow solid, 85.1 g, and the yield is 91%. $^1$H NMR (500 MHz, Chloroform) δ 8.41 (s, 2H), 7.46 (t, J=7.5 Hz, 2H), 7.21 (d, J=7.5 Hz, 4H), 3.00 (hept, J=6.3 Hz, 4H), 1.21 (d, J=6.4 Hz, 24H). Repeat the process above to prepare sufficient amount of N,N'-bis(2,6-diisopropylphenyl)ethanediimine product for future use.

Synthesis of 1,3-bis(2,6-diisopropylphenyl)imidazolium chloride

Add 8.1 g of paraformaldehyde (0.27 mol), 101.5 g of N,N'-bis(2,6-diisopropylphenyl)ethanediimine (0.27 mol) and 1.5 L of ethyl acetate solution in a reactor, heat to 70° C. and mix well. Dropwise add 45.8 g of tetrachloro-silicane slowly with the adding time controlled within 45 min to 1 h, and then keep mixing for 3 h for reaction. Filter the resultant reaction liquid, wash the filter cake with 200 mL of ethyl acetate, and then dry the filter cake to constant weight to get the 1,3-bis(2,6-diisopropylphenyl)imidazolium chloride. The product is grayish white solid, 97.4 g, and the yield is 85%. $^1$H NMR (500 MHz, Chloroform) δ 10.04 (s, 2H), 8.14 (s, 2H), 7.58 (t, J=8.0 Hz, 2H), 7.36 (d, J=7.5 Hz, 4H), 2.43-2.49 (m, 4H), 1.30 (d, J=6.5 Hz, 12H), 1.25 (d, J=7.0 Hz, 12H). Repeat the process above to prepare sufficient amount of 1,3-bis(2,6-diisopropylphenyl)imidazolium chloride as the NHC ligand of the catalyst.

Embodiment 2

Change the addition of 88.5 g of 2,6-diisopropylphenylamine (0.5 mol) in Embodiment 1 to 67.5 g of 2,4,6-trimethylaniline (0.5 mol), and keep other conditions unchanged. Upon reaction, get 64.3 g of N,N'-bis (2,4,6-trimethylphenyl) ethanediimine with the yield up to 88%. $^1$H NMR (500 MHz, Chloroform) δ 7.92 (s, 2H), 7.00 (s, 4H), 2.45 (s, 12H), 2.37 (s, 6H).

Use the N,N'-bis(2,4,6-trimethylphenyl)ethanediimine obtained and paraformaldehyde for reaction under the action of tetrachloro-silicane to get 1,3-bis(2,4,6-trimethylphenyl) imidazolium chloride. $^1$H NMR (500 MHz, Chloroform) δ 6.68 (s, 4H), 5.56 (s, 2H), 4.02 (s, 1H), 2.34 (s, 6H), 2.26 (s, 12H). It can be used as the NHC ligand of the catalyst.

Embodiment 3

Change the addition of 88.5 g of 2,6-diisopropylphenylamine (0.5 mol) in Embodiment 1 to 164.5 g of 2,6-bis(1-phenylpropyl)aniline (0.5 mol), and keep other conditions unchanged; upon reaction, get 147.9 g of N,N'-bis(2, 6-bis(1-phenylpropyl)phenyl)ethanediimine with the yield up to 87%. $^1$H NMR (500 MHz, Chloroform) δ 8.61 (s, 2H), 7.48 (t, J=7.4 Hz, 2H), 7.34-7.23 (m, 20H), 7.22 (t, J=6.9 Hz, 4H), 4.13 (t, J=7.2 Hz, 4H), 1.96 (dd, J=11.4, 4.5 Hz, 4H), 1.92 (dd, J=11.3, 4.5 Hz, 4H), 1.03 (t, J=6.7 Hz, 12H).

Use the N,N'-bis(2, 6-bis(1-phenylpropyl)phenyl)ethanediimine obtained and paraformaldehyde for reaction under the action of tetrachloro-silicane to get 1,3-bis(2,6-bis(1-phenylpropyl)phenyl)imidazolium chloride. $^1$H NMR (500 MHz, Chloroform) δ 7.61-7.20 (m, 21H), 7.13 (d, J=7.3 Hz, 4H), 7.05 (dd, J=8.0, 6.8 Hz, 2H), 5.78 (s, 2H), 4.38 (s, 1H), 4.19-4.12 (m, 4H), 1.99-1.86 (m, 8H), 1.02 (t, J=6.7 Hz, 12H). It can be used as the NHC ligand of the catalyst.

Embodiment 4

Change the addition of 88.5 g of 2,6-diisopropylphenylamine (0.5 mol) in Embodiment 1 to 89.5 g of 2,6- diazadimethylaniline (0.5 mol), and keep other conditions unchanged; upon reaction, get 87.4 g of N,N'-bis(2,6-diazadimethylphenyl)ethanediimine with the yield up to 92%. $^1$H NMR (500 MHz, Chloroform) δ 8.75 (s, 2H), 6.96 (t, J=7.5 Hz, 3H), 6.16 (d, J=7.5 Hz, 4H), 3.03 (s, 24H).

Use the N,N'-bis(2,6-diazadimethylphenyl)ethanediimine obtained and paraformaldehyde for reaction under the action of tetrachloro-silicane to get 1,3-bis(2,6-diazadimethylphenyl)imidazolium chloride. $^1$H NMR (500 MHz, Chloroform) δ 6.55 (t, J=7.5 Hz, 2H), 5.96 (d, J=7.5 Hz, 4H), 5.71 (s, 2H), 4.83 (s, 1H), 3.03 (s, 24H). It can be used as the NHC ligand of the catalyst.

Embodiment 5

Change the addition of 45.8 g of tetrachloro-silicane (0.27 mol) in Embodiment 1 to 67.5 mL of 4M dioxane hydrochloride solution (0.27 mol HCl), and keep other conditions unchanged. Upon reaction, get the target product 1,3-bis(2,6-diisopropylphenyl)imidazolium with the yield up to 50%.

Embodiment 6

Synthesis of Acetophenone Methyl Oxime Palladacycle Dimer

Add 17.7 g of palladium chloride (0.1 mol), 8.5 g of 0.2 lithium chloride (mol) and 500 mL of methanol solution into a reactor flask, and keep blending until full dissolution. Afterwards, add 8.2 g of sodium acetate (0.1 mol) and 14.9 g of acetophenone methyl oxime (0.1 mol), and then keep mixing for 3 days for reaction at the ambient temperature (15-20° C.). Filter the resultant reaction liquid, wash the filter cake with 100 mL of methanol, and then dry the filter cake to constant weight to get the acetophenone methyl oxime palladacycle dimer. The product is yellow-green powder, 23.9 g, and the yield is 83%. $^1$H NMR (500 MHz, Chloroform) δ 7.82-7.80 (m, 2H), 7.57-7.46 (m, 4H), 7.18-7.05 (m, 2H), 3.98 (s, 3H), 3.94 (s, 3H), 2.34 (s, 6H).

Embodiment 7

Change the addition of 14.9 g of acetophenone methyl oxime (0.1 mol) in Embodiment 6 to 13.5 g of acetophenone oxime (0.1 mol), and keep other conditions unchanged; upon reaction, get 22.4 g of acetophenone methyl oxime palladacycle dimer with the yield up to 80%. $^1$H NMR (500 MHz, Chloroform) δ 7.82 (s, 1H), 7.68-7.55 (m, 2H), 7.55-6.72 (m, 2H), 3.37 (s, 3H).

Embodiment 8

Change the addition of 14.9 g of acetophenone methyl oxime (0.1 mol) in Embodiment 6 to 18.1 g of benzaldehyde phenlimino (0.1 mol), and keep other conditions unchanged. Upon reaction, get 27.3 g of benzaldehyde phenlimino palladacycle dimer with the yield up to 84%. $^1$H NMR (500 MHz, Chloroform) δ 8.90 (s, 1H), 7.59 (dd, J=17.1, 9.6 Hz, 5H), 7.49-7.43 (m, 2H), 7.41 (s, 1H), 7.36 (s, 1H), 7.13 (s, 1H).

Embodiment 9

Change the addition of 14.9 g of acetophenone methyl oxime (0.1 mol) in Embodiment 6 to 19.5 g of benzylcarboxaldehyde phenlimino (0.1 mol), and keep other conditions unchanged. Upon reaction, get 24.8 g of Benzylcarboxaldehyde phenlimino palladacycle dimer with the yield up to 74%. $^1$H NMR (500 MHz, Chloroform) δ 7.90 (s, 1H), 7.50-7.38 (m, 2H), 7.38-7.17 (m, 5H), 7.16-7.07 (m, 3H), 3.83 (s, 1H).

Embodiment 10

Synthesis of NHC(IPr)-Acetophenone Methyl Oxime Palladium Catalyst

Under an inert atmosphere, add 29.0 g of acetophenone methyl oxime palladacycle dimer (0.05 mol), 5.6 g of potassium tert-butoxide (0.05 mol) and 230 mL of anhydrous tetrahydrofuran solution into a reactor. Afterwards, add 42.5 g of 1,3-bis(2,6-diisopropylphenyl)imidazolium (0.1 mol), and keep mixing the resultant reaction liquid for 24 h for reaction at the ambient temperature (15-20° C.). Filter the resultant reaction liquid, wash with 100 mL of ethyl acetate, combine the filtrate, remove the solvent and then dry to get the target product NHC(IPr)-acetophenone methyl oxime palladium catalyst. The product is bright yellow solid, 30.2 g, and the yield is 44%. $^1$H NMR (500 MHz, Chloroform) δ 7.38 (t, J=7.8 Hz, 2H), 7.31-7.29 (m, 2H), 7.23 (s, 2H), 7.17-7.16 (m, 2H), 7.08-7.06 (m, 1H), 6.90 (dt, J=25, 7.5 Hz 2H), 6.70 (d, J=7.5 Hz, 1H), 3.84 (s, 3H), 3.41-3.17 (m, 4H), 2.16 (s, 3H), 1.48 (d, J=6.5 Hz, 6H), 1.14 (d, J=7.0 Hz, 6H), 1.00 (d, J=7.0 Hz, 6H), 0.80 (d, J=6.5 Hz, 6H).

Embodiment 11

Synthesis of NHC(IPr)-Acetophenone Oxime Palladium Catalyst

Change the addition of 29.0 g of acetophenone methyl oxime palladacycle dimer (0.05 mol) in Embodiment 10 to 27.6 g of acetophenone oxime palladacycle dimer (0.05 mol), and keep other conditions unchanged. Upon reaction, get NHC(IPr)-acetophenone oxime palladium catalyst. The product is yellow powder, 30.4 g, and the yield is 53%. $^1$H NMR (500 MHz, Chloroform) δ 10.46 (s, 1H), 7.42 (t, J=7.8 Hz, 2H), 7.32-7.31 (m, 2H), 7.24 (s, 2H), 7.20-7.19 (m, 2H), 6.93-6.88 (m, 2H), 6.80 (dt, J=7.3, 2.0 Hz 1H), 6.61 (d, J=7.0 Hz, 1H), 3.24-3.09 (m, 4H), 2.06 (s, 3H), 1.46 (d, J=6.5 Hz, 6H), 1.18 (d, J=7.0 Hz, 6H), 1.00 (d, J=7.0 Hz, 6H), 0.81 (d, J=7.0 Hz, 6H).

Embodiment 12

Change the addition of 29.0 g of acetophenone methyl oxime (0.05 mol) in Embodiment 10 to 32.2 g of benzaldehyde phenlimino palladacycle dimer (0.05 mol), and keep other conditions unchanged. Upon reaction, get NHC(IPr)-benzaldehyde phenlimino palladium catalyst. The product is yellow powder, 34.3 g, and the yield is 48%. $^1$H NMR (500 MHz, Chloroform) δ 8.68 (s, 1H), 7.44 (dddd, J=15.5, 9.5, 8.9, 4.4 Hz, 5H), 7.77-6.61 (m, 16H), 7.52-6.61 (m, 12H), 7.36-5.60 (m, 10H), 7.01 (dd, J=8.0, 7.0 Hz, 2H), 7.07-5.60 (m, 5H), 5.73 (s, 2H), 3.23 (hept, J=6.3 Hz, 4H), 1.47 (d, J=6.5 Hz, 6H), 1.16 (d, J=7.0 Hz, 6H), 1.00 (d, J=7.0 Hz, 6H), 0.80 (d, J=6.5 Hz, 6H).

Embodiment 13

Synthesis of NHC(IMes)-Acetophenone Methyl Oxime Palladium Catalyst

Change the addition of 42.5 g of 1,3-bis(2,6-diisopropylphenyl)imidazolium (0.1 mol) in Embodiment 10 to 34.9 g of 1,3-bis(2,4,6-trimethylphenyl)imidazolium, and keep other conditions unchanged. Upon reaction, get NHC (IMes)-acetophenone methyl oxime palladium catalyst. The product is bright yellow solid 29.0 g, and the yield is 44%. $^1$H NMR (500 MHz, Chloroform) δ 8.51-6.88 (m, 4H), 7.46 (dqd, J=16.5, 7.5, 1.6 Hz, 2H), 7.46 (dqd, J=16.5, 7.5, 1.6 Hz, 2H), 6.79 (s, 4H), 5.72 (s, 2H), 3.82 (s, 3H), 3.33 (s, 3H), 2.35 (s, 6H), 2.27 (s, 12H).

Embodiment 14

Application in Suzuki-Miyaura Coupling Reaction

Under an inert atmosphere, add 12.6 g of o-chlorotoluene (0.1 mol), 12.2 g of phenylboronic acid (0.1 mol), 8.4 g of potassium hydroxide (0.15 mol), 500 ppm of the NHC type palladium catalyst indicated in Formula (X) or (XI) and 10 mL of isopropanol into a reactor. After mixing for 2 h for reaction at a temperature of 80° C., stop reaction. Remove the solvent of the resultant reaction liquid to get the crude product with the gas-phase yield more than 99%. Upon column chromatographic purification, obtain 16.1 g of the target product with the isolated yield up to 95%. $^1$H NMR (500 MHz, Chloroform) δ 7.63 (s, 1H), 7.46 (t, J=8.8 Hz, 3H), 7.39-7.30 (m, 5H), 2.23 (s, 3H).

Embodiment 15

Change the addition of 18.1 g of o-chlorotoluene (0.1 mol) in Embodiment 14 to 22.2 g of p-chlorbenzotrifluorid, and keep other conditions unchanged. Upon column chromatographic purification, obtain 21.5 g of the target product with the isolated yield up to 97%. $^1$H NMR (500 MHz, Chloroform) δ 7.79-7.62 (m, 4H), 7.52-7.36 (m, 5H).

Embodiment 16

Change the addition of 18.1 g of o-chlorotoluene (0.1 mol) in Embodiment 14 to 16.2 g of α-chloronaphthalene (0.1 mol), and keep other conditions unchanged. Upon column chromatographic purification, obtain 17.9 g of the target product with the isolated yield up to 88%. $^1$H NMR (500 MHz, Chloroform) δ 8.58 (m, 1H), 8.24 (dd, J=7.5, 1.4 Hz, 1H), 7.89 (m, 3H), 7.76 (m, 3H), 7.69 (d, J=7.5 Hz, 1H), 7.40 (m, 7H).

Embodiment 17

Change the addition of 18.1 g of o-chlorotoluene (0.1 mol) in Embodiment 14 to 11.3 g of 3-chloropyridine (0.1 mol), and keep other conditions unchanged. Upon column chromatographic purification, obtain 14.4 g of the target product with the isolated yield up to 93%. $^1$H NMR (500 MHz, Chloroform) δ 8.94 (d, J=1.3 Hz, 1H), 8.58 (dd, J=7.5, 1.3 Hz, 1H), 8.24 (dt, J=7.5, 1.6 Hz, 1H), 7.46 (m, 6H).

Embodiment 18

Change the addition of 12.2 g of phenylboronic acid (0.1 mol) in Embodiment 14 to 15.0 g of 3,5-dimethyl phenylboronic acid (0.1 mol), and keep other conditions unchanged. Upon column chromatographic purification, obtain 18.2 g of the target product with the isolated yield up to 93%. $^1$H NMR (500 MHz, Chloroform) δ 7.68 (d, J=1.4 Hz, 2H), 7.54 (d, J=7.5 Hz, 2H), 7.40 (t, J=1.4 Hz, 1H), 7.19 (d, J=7.5 Hz, 2H), 2.44 (s, 6H), 2.42 (s, 3H).

Embodiment 19

Application in Heck Reaction

Under an inert atmosphere, add 14.3 g of p-chloroanisole (0.1 mol), 12.8 g of tert-Butyl acrylate (0.1 mol), 500 ppm of the NHC type palladium catalyst indicated in Formula (X) or (XI) and 10 mL of N, N-dimethylacetamide into a reactor; keep mixing for 10 h for reaction at a temperature of 120° C.; remove the solvent of the resultant reaction liquid to get the crude product. Upon column chromatographic purification, obtain 19.2 g of the target product with the isolated yield up to 82%. $^1$H NMR (500 MHz, Chloroform) δ 7.84 (d, J=7.5 Hz, 2H), 7.69 (d, J=15.0 Hz, 1H), 7.22 (d, J=7.5 Hz, 2H), 6.45 (d, J=15.2 Hz, 1H), 3.87 (s, 3H), 1.47 (s, 9H).

Embodiment 20

Change the addition of 12.8 g of tert-Butyl acrylate (0.1 mol) in Embodiment 19 to 8.6 g of methyl acrylate (0.1 mol), and keep other conditions unchanged. Upon column chromatographic purification, obtain 16.3 g of the target product with the isolated yield up to 85%. $^1$H NMR (500 MHz, Chloroform) δ 7.84 (d, J=7.5 Hz, 2H), 7.69 (d, J=15.0 Hz, 1H), 7.22 (d, J=7.3 Hz, 2H), 6.45 (d, J=15.2 Hz, 1H), 3.87 (s, 3H), 3.84 (s, 3H).

Embodiment 21

Change the addition of 14.3 g of p-chloroanisole (0.1 mol) in Embodiment 19 to 14.1 g of 3,5-dimethylchlorobenzene (0.1 mol) and the addition of 12.8 g of tert-Butyl acrylate (0.1 mol) to 10.4 g of styrene (0.1 mol), and keep other conditions unchanged. Upon column chromatographic purification, obtain 18.3 g of the target product with the isolated yield up to 88%. $^1$H NMR (500 MHz, Chloroform) δ 7.63 (dd, J=7.5, 1.3 Hz, 2H), 7.42 (t, J=7.5 Hz, 2H), 7.32-7.23 (m, 1H), 7.22-7.14 (m, 4H), 2.43 (s, 6H).

Embodiment 22

Change the addition of 14.3 g of p-chloroanisole (0.1 mol) in Embodiment 19 to 16.2 g of α-chloronaphthalene (0.1 mol), and keep other conditions unchanged. Upon column chromatographic purification, obtain 20.1 g of the target product with the isolated yield up to 79%. $^1$H NMR (500 MHz, Chloroform) δ 7.99 (m, 1H), 7.87 (m, 2H), 7.73 (m, 3H), 7.61 (td, J=7.5, 1.4 Hz, 1H), 7.44 (td, J=7.5, 1.4 Hz, 1H), 6.41 (d, J=15.0 Hz, 1H), 1.48 (s, 9H).

Embodiment 23

Application in Buchwald-Hartwig Reaction

Under an inert atmosphere, add 14.2 g of p-chloroanisole (0.1 mol), 9.9 g of cyclohexylamine (0.1 mol), 16.8 g of potassium tert-butoxide (0.15 mol), 500 ppm of the NHC type palladium catalyst indicated in Formula (X) or (XI) and 15 mL of N, N-dimethylfomamide solution into a reactor. Keep mixing for 5 h for reaction at a temperature of 80° C.; remove the solvent of the resultant reaction liquid to get the crude product. Upon column chromatographic purification, obtain 17.4 g of the target product with the isolated yield up to 85%. $^1$H NMR (500 MHz, Chloroform) δ 6.70 (m, 4H), 3.89 (s, 1H), 3.87 (s, 3H), 3.01 (p, J=7.3 Hz, 1H), 1.94 (dt, J=7.3, 5.7 Hz, 2H), 1.73 (m, 3H), 1.37 (m, 5H).

Embodiment 24

Change the addition of 14.2 g of p-chloroanisole (0.1 mol) in Embodiment 23 to 15.4 g of 2,4,6-trimethylchlorobenzene and the addition of 9.9 g of cyclohexylamine (0.1 mol) to 9.3 g of aniline (0.1 mol), and keep other conditions unchanged. Upon column chromatographic purification, obtain 19.2 g of the target product with the isolated yield up to 91%. $^1$H NMR (500 MHz, Chloroform) δ 7.32 (dd, J=16.1, 8.6 Hz, 3H), 7.14 (dd, J=7.5, 1.4 Hz, 2H), 6.95 (tt, J=7.6, 1.4 Hz, 1H), 6.83 (s, 2H), 2.35 (s, 3H), 2.20 (s, 6H).

Embodiment 25

Change the addition of 9.9 g of cyclohexylamine (0.1 mol) in Embodiment 23 to 8.7 g of morpholine (0.1 mol), and keep other conditions unchanged. Upon column chromatographic purification, obtain 17.0 g of the target product with the isolated yield up to 88%. $^1$H NMR (500 MHz, Chloroform) δ 6.87 (d, J=7.5 Hz, 1H), 6.70 (d, J=7.5 Hz, 1H), 3.85 (dd, J=12.8, 6.5 Hz, 4H), 3.46 (t, J=6.2 Hz, 1H), 3.14 (t, J=6.1 Hz, 1H).

Embodiment 26

Change the addition of 14.2 g of p-chloroanisole (0.1 mol) in Embodiment 23 to 16.2 g of 1-chloronaphthalene (0.1 mol) and the addition of 9.9 g of cyclohexylamine (0.1 mol) to 7.3 g of diethylamine (0.1 mol), and keep other conditions unchanged. Upon column chromatographic purification, obtain 16.5 g of the target product with the isolated yield up to 83%. $^1$H NMR (500 MHz, Chloroform) δ 8.31 (m, 1H), 7.64 (m, 4H), 7.40 (m, 1H), 7.20 (m, 1H), 3.72 (q, J=6.3 Hz, 2H), 3.56 (q, J=6.2 Hz, 2H), 1.21 (t, J=6.3 Hz, 6H).

Embodiment 27

Application in Sonogashira Reaction

Under an inert atmosphere, add 14.9 g of cyclopentane bromide (0.1 mol), 10.8 g of cyclohexane acetylene (0.1 mol), 29.0 g of caesium carbonate (0.15 mol), 500 ppm of the NHC type palladium catalyst indicated in Formula (X) or (XI), 2000 ppm of copper iodide and 15 mL of N, N-dimethylfomamide solution into a reactor; keep mixing for 10 h for reaction at a temperature of 60° C.; remove the solvent of the resultant reaction liquid to get the crude product. Upon column chromatographic purification, obtain 8.4 g of the target product with the isolated yield up to 48%. $^1$H NMR (500 MHz, Chloroform) δ 2.55 (m, 1H), 2.47 (pd, J=7.8, 2.6 Hz, 1H), 2.01 (dt, J=7.9, 5.7 Hz, 2H), 1.77 (m, 9H), 1.53 (m, 4H), 1.35 (m, 3H).

Embodiment 28

Change the addition of 10.8 g of cyclohexane acetylene (0.1 mol) in Embodiment 27 to 6.8 g of 1-pentyne, and keep other conditions unchanged. Upon column chromatographic purification, obtain 7.8 g of the target product with the isolated yield up to 57%. $^1$H NMR (500 MHz, Chloroform) δ 2.55 (m, 1H), 2.34 (td, J=5.4, 2.5 Hz, 2H), 1.80 (dddd, J=12.0, 9.0, 4.6, 2.0 Hz, 4H), 1.73 (dtd, J=7.1, 3.8, 1.9 Hz, 2H), 1.68 (m, 2H), 1.54 (tdd, J=6.9, 3.1, 2.0 Hz, 2H), 1.12 (t, J=6.6 Hz, 3H).

Embodiment 29

Change the addition of 14.9 g of cyclopentane bromide (0.1 mol) in Embodiment 27 to 17.1 g of benzyl bromide (0.1 mol) and the addition of 10.8 g of cyclohexane acetylene (0.1 mol) to 10.2 g of phenylacetylene (0.1 mol), and keep other conditions unchanged. Upon column chromatographic purification, obtain 13.2 g of the target product with the isolated yield up to 69%. $^1$H NMR (500 MHz, Chloroform) δ 7.52 (m, 2H), 7.37 (m, 3H), 7.21 (m, 5H), 3.77 (s, 2H).

Embodiment 30

Application in Kumada-Tamao-Corriu Reaction

Under an inert atmosphere, add 15.5 g of 2, 4, 6-trimethylchlorobenzene (0.1 mol), 35.7 mL of Naphthyl Grignard reagent (0.1 mol, 2.8 m of ether solution), 500 ppm of the NHC type palladium catalyst indicated in Formula (X) or (XI) and 10 mL of anhydrous tetrahydrofuran solution into a reactor; keep mixing for 24 h for reaction at a temperature of 50° C.; remove the solvent of the resultant reaction liquid to get the crude product. Upon column chromatographic purification, obtain 22.6 g of the target product with the isolated yield up to 92%. $^1$H NMR (500 MHz, Chloroform) δ 7.98 (m, 3H), 7.69 (t, J=1.5 Hz, 1H), 7.56 (m, 2H), 7.44 (dd, J=7.4, 1.5 Hz, 1H), 7.03 (s, 2H), 2.83 (s, 6H), 2.52 (s, 3H).

Embodiment 31

Change the addition of 15.5 g of 2, 4, 6-trimethylchlorobenzene (0.1 mol) in Embodiment 30 to 11.9 g of 2-chlorothiophene (0.1 mol) and the addition of 35.7 mL of Naphthyl Grignard reagent (0.1 mol, 2.8 m of ether solution) to 35.7 mL of Methoxyphenyl Grignard reagent (0.1 mol, 2.8 m of ether solution), and keep other conditions unchanged. Upon column chromatographic purification, obtain 13.1 g of the target product with the isolated yield up to 69%. $^1$H NMR (500 MHz, Chloroform) δ 7.76 (dd, J=7.5, 1.4 Hz, 1H), 7.45 (m, 3H), 7.12 (m, 3H), 3.88 (s, 3H).

Embodiment 32

Change the addition of 35.7 mL of Naphthyl Grignard reagent (0.1 mol, 2.8 m of ether solution) to 35.7 mL of furan Grignard reagent (0.1 mol, 2.8 m of ether solution), and keep other conditions unchanged; upon column chromatographic purification, obtain 13.4 g of the target product with the isolated yield up to 72%. $^1$H NMR (500 MHz, Chloroform) δ 7.59 (dd, J=7.5, 1.4 Hz, 1H), 7.04 (s, 2H), 6.93 (dd, J=7.5, 1.4 Hz, 1H), 6.49 (t, J=7.4 Hz, 1H), 2.64 (s, 6H), 2.52 (s, 3H).

Embodiment 33

Application in Negishi Reaction

Under an inert atmosphere, add 14.0 g of 2,6-dimethylchlorobenzene (0.1 mol), 50 mL of tetrahydrofuran solution of phenyl zinc chloride (0.1 mol, 2.8 m of tetrahydrofuran solution) and 500 ppm of the palladium catalyst indicated in Formula (X) or (XI) into a reactor; keep mixing for 1-3 h for reaction at a temperature of 25° C.-50° C.; remove the solvent of the resultant reaction liquid to get the crude product. Upon column chromatographic purification, obtain 14.1 g of the target product with the isolated yield up to 82%. $^1$H NMR (500 MHz, Chloroform) δ 7.61 (dd, J=7.5, 1.4 Hz, 1H), 7.47 (t, J=7.5 Hz, 1H), 7.21 (d, J=7.5 Hz, 2H), 6.94 (dd, J=7.5, 1.6 Hz, 1H), 6.50 (t, J=7.5 Hz, 1H), 2.63 (s, 6H).

Embodiment 34

Change the addition of 14.0 g of 2,6-dimethylchlorobenzene (0.1 mol) in Embodiment 33 to 16.2 g of chloronaphthalene (0.1 mol), and keep other conditions unchanged. Upon column chromatographic purification, obtain 20.2 g of the target product with the isolated yield up to 87%. $^1$H NMR (500 MHz, Chloroform) δ 8.48 (m, 1H), 7.96 (m, 3H), 7.70 (t, J=7.5 Hz, 1H), 7.41 (m, 3H), 7.21 (d, J=7.5 Hz, 2H), 2.56 (s, 6H).

Embodiment 35

Change the addition of 14.0 g of 2,6-dimethylchlorobenzene (0.1 mol) in Embodiment 33 to 11.2 g of chlorobenzene (0.1 mol) and the addition of 50 mL of tetrahydrofuran solution of phenyl zinc chloride (0.1 mol, 2.8 m of tetrahydrofuran solution) to 50 mL of tetrahydrofuran solution of benzyl zinc chloride (0.1 mol, 2.8 m of tetrahydrofuran solution), and keep other conditions unchanged. Upon column chromatographic purification, obtain 14.9 g of the target product with the isolated yield up to 79%. $^1$H NMR (500 MHz, Chloroform) δ 7.25 (m, 10H), 3.86 (s, 2H).

Embodiment 36

Change the addition of 14.0 g of 2,6-dimethylchlorobenzene (0.1 mol) in Embodiment 33 to 11.2 g of chlorobenzene (0.1 mol) and the addition of 50 mL of tetrahydrofuran solution of phenyl zinc chloride (0.1 mol, 2.8 m of tetrahydrofuran solution) to 50 mL of tetrahydrofuran solution of homoallylic zinc chloride (0.1 mol, 2.8 m of tetrahydrofuran solution), and keep other conditions unchanged. Upon column chromatographic purification, obtain 9.9 g of the target product with the isolated yield up to 75%. $^1$H NMR (500 MHz, Chloroform) δ 7.21 (m, 5H), 5.76 (ddt, J=16.4, 10.1, 6.2 Hz, 1H), 4.99 (m, 2H), 2.59 (t, J=7.9 Hz, 2H), 2.33 (dd, J=14.3, 7.7 Hz, 2H).

Embodiment 37

Application of α-Ketone Acylation

Under an inert atmosphere, add 16.2 g of 1-chloronaphthalene (0.1 mol), 13.4 g of propiophenone (0.1 mol), 14.4 g of sodium tert-butoxide, 500 ppm of NHC(IPr)-acetophenone methyl oxime palladium catalyst and 10 mL of toluene into a reactor; keep mixing for 10 h for reaction at a temperature of 60° C.; remove the solvent of the resultant reaction liquid to get the crude product. Upon column chromatographic purification, obtain 21.8 g of the target product with the isolated yield up to 84%. $^1$H NMR (500 MHz, Chloroform) δ 7.84 (m, 5H), 7.62 (t, J=1.4 Hz, 1H), 7.51 (m, 6H), 4.63 (q, J=6.4 Hz, 1H), 1.70 (d, J=6.6 Hz, 3H).

Embodiment 38

Change the addition of 16.2 g of 1-chloronaphthalene (0.1 mol) in Embodiment 24 to 14.1 g of 2,6-dimethylchlorobenzene (0.1 mol) and the addition of 13.4 g of propiophenone (0.1 mol) to 14.6 g of 1-tetralone (0.1 mol), and keep other conditions unchanged. Upon column chromatographic purification, obtain 19.5 g of the target product with the isolated yield up to 78%. $^1$H NMR (500 MHz, Chloroform) δ 7.57 (dd, J=7.4, 1.5 Hz, 1H), 7.39 (td, J=7.6, 1.8 Hz, 2H), 7.26 (m, 4H), 4.28 (t, J=8.8 Hz, 1H), 2.81 (m, 2H), 2.40 (s, J=8.0 Hz, 6H), 2.36 (m, 1H), 2.11 (ddd, J=12.5, 7.7, 5.3 Hz, 1H).

What is claimed is:

1. An n-heterocyclic carbene (NHC) type palladium catalyst having the following molecular structure:

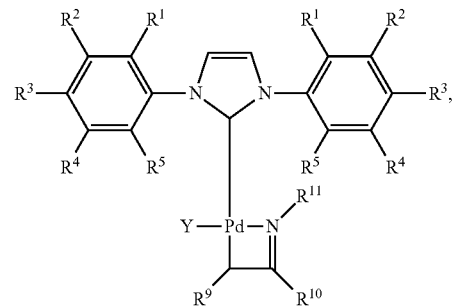

where $R^1$, $R^2$, $R^3$, $R^4$ and $R^5$ each independently represent H, alkyl, heteroalkyl, or aryl; $R^9$ represents alkyl or arylalkenyl; $R^{10}$ and $R^{11}$ each independently represent H, alkyl, heteroalkyl, or aryl; and Y represents Cl or OAc.

2. The NHC type palladium catalyst as claimed in claim 1, wherein $R^1$, $R^3$ and $R^5$ each independently represent H, linear or branched $C_1$-$C_{15}$ alkyl, or linear or branched aza-oxa-$C_1$-$C_{15}$ alkyl.

3. The NHC type palladium catalyst as claimed in claim 1,
wherein $R^9$ represents H, linear or branched $C_1$-$C_{10}$ alkyl, linear or branched $C_1$-$C_{10}$ alkenyl, or linear or branched $C_1$-$C_{10}$ allyl; $R^{10}$ and $R^{11}$ each independently represent H, hydroxyl, alkoxy, linear or branched $C_1$-$C_{10}$ alkyl, or substituted or unsubstituted $C_6$-$C_{18}$ aryl; and
wherein the substituted or unsubstituted $C_6$-$C_{18}$ aryl is selected from the group consisting of phenyl, 1-naphthyl, 4-tert-butyl-phenyl, 3,5-di-tert-butyl-phenyl, 4-methylphenyl, 3,5-dimethylphenyl, 4,4'-biphenyl, and 3,5-diphenyl-phenyl.

4. A preparation method of the NHC type palladium catalyst according to claim 1, comprising:
(a) cyclizing glyoxaldiimine indicated in Formula (II) and paraformaldehyde under an action of additive (III) to form a NHC type compound indicated in Formula (IV),

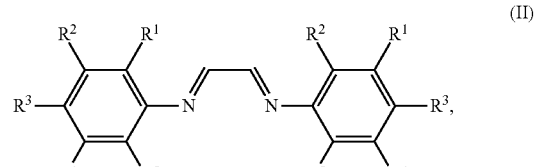

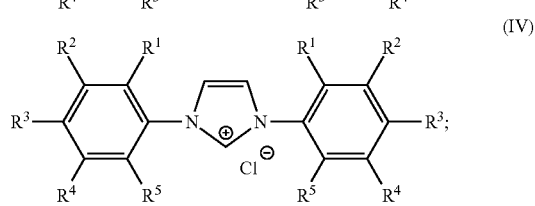

(b) obtaining palladium$^{(II)}$ cyclic dimer indicated in Formula (IX) from a reaction of palladium$^{(II)}$ and a compound containing carbon-nitrogen double bonds indicated in Formula (VII) under an action of inorganic salt (V),

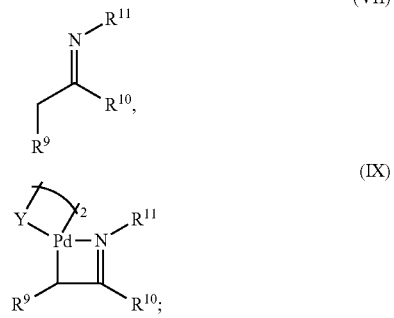

and
(c) coordinating the palladium$^{(II)}$ cyclic dimer indicated in Formula (IX) and the NHC type compound indicated in Formula (IV) under an alkaline condition to obtain the NHC type palladium catalyst of claim 1,
wherein the additive (III) is at least one selected from the group consisting of dioxane hydrochloride, tetrachlorosilicane, and trimethyl chlorosilane;
the palladium$^{(II)}$ in step (b) is at least one selected from the group consisting of palladium chloride, palladium acetate, palladium nitrate, and palladium acetylacetonate; and
the inorganic salt (V) is at least one selected from the group consisting of lithium chloride, sodium bromide, sodium iodide, and sodium acetate.

5. The preparation method of the NHC type palladium catalyst as claimed in claim 4,
wherein, in step (c), the coordinating is conducted in an air-isolated condition, the alkaline condition contains at least one base that is selected from the group consisting of potassium tert-butoxide, sodium tert-butoxide, potassium hydroxide, sodium ethoxide, potassium carbonate, and sodium acetate.

6. The NHC type palladium catalyst according to claim 1, wherein the NHC type palladium catalyst catalyzes at least one coupling reaction selected from the group consisting of Suzuki-Miyaura, Heck, Buchwald-Hartwig, Kumada-Tamao-Corriu, Sonogashira, Negishi, and α-ketone arylation.

7. The NHC type palladium catalyst as claimed in claim 6,
wherein the NHC type palladium catalyst in the coupling reaction of Suzuki-Miyaura catalyzes a cross-coupling reaction between halogenated aromatic hydrocarbon represented by Ar—$X^1$ and arylboronic acid represented by (HO)$_2$B—Ar' under an action of a base to obtain a compound indicated by Formula E: Ar—Ar', where Ar and Ar' each independently represent substituted or unsubstituted $C_6$-$C_{18}$ aryl, $C_4$-$C_{10}$ aza-polycyclic aromatic hydrocarbon, $C_4$-$C_{10}$ oxa-polycyclic aromatic hydrocarbon, or $C_4$-$C_{10}$ thiox-polycyclic aromatic hydrocarbon; $X^1$ is Cl, Br, I, or OTf; and the base is at least one base selected from the group consisting of potassium tert-butoxide, sodium tert-butoxide, potassium hydroxide, sodium hydroxide, potassium phosphate, potassium carbonate, sodium carbonate, and sodium methoxide.

8. The NHC type palladium catalyst as claimed in claim 6, wherein the NHC type palladium catalyst in the coupling reaction of Heck catalyzes a coupling reaction between halogenated aromatic hydrocarbon represented by Ar—$X^2$ and alkene represented by $CH_2$=CH—$R^{12}$ to obtain a compound indicated by Formula F:

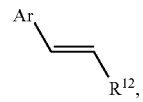

where Ar represents substituted or unsubstituted $C_6$-$C_{18}$ aryl; $R^{12}$ represents substituted or unsubstituted $C_6$-$C_{18}$ aryl, ester or benzyl containing methyl ester, ethyl ester, isopropyl ester, or tert-butyl ester; and $X^2$ is Cl, Br, I, or OTf.

9. The NHC type palladium catalyst as claimed in claim 6, wherein the NHC type palladium catalyst in the coupling reaction of Buchwald-Hartwig catalyzes a coupling reaction between halogenated aromatic hydrocarbon represented by Ar—$X^3$ and primary or secondary amine represented by $R^{13}$—NH—$R^{14}$ under an action of a base to obtain a compound indicated by Formula G:

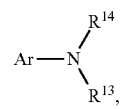

where Ar represents substituted or unsubstituted $C_6$-$C_{18}$ aryl; $R^{13}$ and $R^{14}$ each independently represent H, $C_1$-$C_6$ alkyl or cycloalkyl, substituted or unsubstituted $C_6$-$C_{18}$ aryl, or linked pyranoid carbocycle, pyranoid oxa-carbocycle or pyranoid aza-carbocycle; $X_3$ is Cl, Br, I, or OTf, and
wherein the base is at least one base selected from the group consisting of potassium tert-butoxide, sodium tert-butoxide, potassium hydroxide, sodium hydroxide, potassium phosphate, potassium carbonate, sodium carbonate, and sodium methoxide.

10. The NHC type palladium catalyst as claimed in claim 6, wherein the NHC type palladium catalyst in the coupling reaction of Sonogashira catalyzes a coupling reaction between halogenated aromatic hydrocarbon represented by $R^{15}$—$X^4$ and terminal alkyne represented by

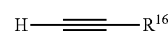

under an action of a base to obtain a compound indicated by Formula H:

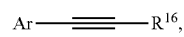

where $R^{15}$ represents $C_1$-$C_{10}$ alkyl or cycloalkyl; $R^{16}$ represents substituted or unsubstituted $C_6$-$C_{18}$ aryl, linear $C_1$-$C_{10}$ alkyl, branched $C_1$-$C_{10}$ alkyl, or $C_1$-$C_{10}$ cycloalkyl or alkoxy; $X^4$ is Cl, Br, I, or OTf, and
wherein the base is at least one base selected from the group consisting of potassium tert-butoxide, sodium tert-butoxide, potassium hydroxide, sodium hydroxide, potassium phosphate, potassium carbonate, sodium carbonate, and sodium methoxide.

11. The NHC type palladium catalyst as claimed in claim 6, wherein the NHC type palladium catalyst in the coupling reaction of Kumada-Tamao-Corriu catalyzes a coupling reaction between halogenated aromatic hydrocarbon represented by Ar—$X^5$ and aryl Grignard reagent represented by $R^{17}$MgBr to obtain a compound represented by Formula I: Ar—$R^{17}$, where Ar represents substituted or unsubstituted $C_6$-$C_{18}$ aryl; $R^{17}$ represents substituted or unsubstituted $C_6$-$C_{18}$ aryl, furanoid or pyranoid aza-heterocyclic aryl, furanoid or pyranoid oxa-heterocyclic aryl, or furanoid thia-heterocyclic aryl; and $X^5$ is Cl, Br, I, or OTf.

12. The NHC type palladium catalyst as claimed in claim 6, wherein the NHC type palladium catalyst in the coupling reaction of Negishi catalyzes a coupling reaction between halogenated aromatic hydrocarbon represented by Ar—$X^6$ and organic zinc reagent represented by $R^{18}$ZnCl to obtain a compound indicated by Formula J: Ar—$R^{18}$, where Ar represents substituted or unsubstituted $C_6$-$C_{18}$ aryl; $R^{18}$ represents substituted or unsubstituted $C_6$-$C_{18}$ aryl, benzyl or homoallyl; and $X^6$ is Cl, Br, I, or OTf.

13. The NHC type palladium catalyst as claimed in claim 6, wherein the NHC type palladium catalyst in the coupling reaction of α-ketone arylation catalyzes a coupling reaction between halogenated aromatic hydrocarbons represented by Ar—$X^7$ and α-ketone represented by

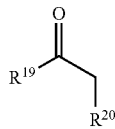

to obtain a compound indicated by Formula K:

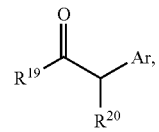

where Ar represents substituted or unsubstituted $C_6$-$C_{18}$ aryl; $R^{19}$ represents substituted or unsubstituted $C_6$-$C_{18}$ aryl, furanoid or pyranoid aza-heterocyclic aryl, furanoid or pyranoid oxa-heterocyclic aryl, or furanoid thia-heterocyclic aryl; $R^{29}$ represents linear $C_1$-$C_6$ alkyl, branched $C_1$-$C_6$ alkyl, or $C_1$-$C_6$ cycloalkyl; and $X^7$ is Cl, Br, I, or OTf,
wherein $R^{19}$ and $R^{20}$ are optionally linked to form a ring; and the base is at least one base selected from the group consisting of potassium tert-butoxide, sodium tert-butoxide, potassium hydroxide, sodium hydroxide, potassium phosphate, potassium carbonate, sodium carbonate, and sodium methoxide.

14. The NHC type palladium catalyst as claimed in claim 1, wherein $R^1$, $R^3$ and $R^5$ each independently represent H, linear or branched alkyl $C_1$-$C_{10}$, or linear or branched aza-oxa-$C_1$-$C_{10}$ alkyl.

15. The NHC type palladium catalyst as claimed in claim 14, wherein the linear or branched $C_1$-$C_{10}$ alkyl contains methyl, ethyl, isopropyl, isobutyl, 1-ethylpropyl, 1-phenylpropyl, or cyclohexyl; and the linear or branched aza-oxa $C_1$-$C_{10}$ alkyl contains N-dimethyl, N-diethyl, methoxyl, or ethyoxyl.

16. The NHC type palladium catalyst as claimed in claim 3, wherein $R^9$ represents H, methyl, or methylene.

* * * * *